United States Patent
Lee et al.

(10) Patent No.: US 11,203,292 B2
(45) Date of Patent: Dec. 21, 2021

(54) VEHICLE AND CONTROL METHOD FOR THE SAME

(71) Applicants: Hyundai Motor Company, Seoul (KR); Kia Motors Corporation, Seoul (KR)

(72) Inventors: Jinmo Lee, Gyeonggi-do (KR); Kaangdok Yee, Gyeonggi-do (KR); Jung Keun You, Gyeonggi-do (KR); Joongkwan Kim, Gyeonggi-do (KR)

(73) Assignees: Hyundai Motor Company, Seoul (KR); Kia Motors Corporation, Seoul (KR)

(*) Notice: Subject to any disclaimer, the term of this patent is extended or adjusted under 35 U.S.C. 154(b) by 108 days.

(21) Appl. No.: 16/693,239

(22) Filed: Nov. 23, 2019

(65) Prior Publication Data

US 2020/0215970 A1    Jul. 9, 2020

(30) Foreign Application Priority Data

Jan. 7, 2019 (KR) .......... 10-2019-0001744

(51) Int. Cl.
*B60Q 9/00* (2006.01)
*A61B 5/00* (2006.01)
(Continued)

(52) U.S. Cl.
CPC .......... *B60Q 9/00* (2013.01); *A61B 5/165* (2013.01); *A61B 5/18* (2013.01); *A61B 5/6893* (2013.01);
(Continued)

(58) Field of Classification Search
CPC .......... B60Q 9/00; A61B 5/743; A61B 5/744; A61B 5/165; A61B 5/7455; A61B 5/7405; A61B 5/18; A61B 5/6893; A61B 5/0533; A61B 5/0077; A61B 5/369; B60N 2/90; B60N 2002/981; B60H 2001/00733; B60H 1/00742; B60H 3/0007; B60H 1/00828; B60R 1/00; G06F 3/015; G06F 3/013; G06F 3/016; G06F 3/011; G06F 2203/011; B60K 2370/21; B60K 37/06; B60W 2540/22; G06K 9/6273; G06K 9/00845; G06K 9/00832; G06K 9/00302

See application file for complete search history.

(56) References Cited

U.S. PATENT DOCUMENTS 8,004,391 B2 * 8/2011 Cruz Hernandez .......... A61B 5/02438
340/407.1
8,764,656 B2 * 7/2014 Shin .......... A61B 5/1123
600/301
(Continued)

*Primary Examiner* — Toan N Pham
(74) *Attorney, Agent, or Firm* — Mintz Levin Cohn Ferris Glovsky and Popeo, P.C.; Peter F. Corless

(57) ABSTRACT

A vehicle is provided to include a bio-signal sensor that detects a bio-signal of a user, a display device that displays an image and a controller that determines at least one of a positivity of the user or change amount of the positivity of the user based on the detected bio-signal. The controller accumulates a positivity index when at least one of the positivity or change amount of the positivity is equal to or greater than a predetermined positivity or a predetermined change amount of the positivity and transmit a control signal to the display device to display the accumulated positivity index.

18 Claims, 11 Drawing Sheets

(51) Int. Cl.

| | |
|---|---|
| *A61B 5/16* | (2006.01) |
| *A61B 5/18* | (2006.01) |
| *B60N 2/90* | (2018.01) |
| *B60H 3/00* | (2006.01) |
| *B60H 1/00* | (2006.01) |
| *B60R 1/00* | (2006.01) |
| *G06F 3/01* | (2006.01) |
| *G06K 9/00* | (2006.01) |

(52) U.S. Cl.
CPC ............. *A61B 5/743* (2013.01); *A61B 5/744* (2013.01); *A61B 5/7405* (2013.01); *A61B 5/7455* (2013.01); *B60H 1/00828* (2013.01); *B60H 3/0007* (2013.01); *B60N 2/90* (2018.02); *B60R 1/00* (2013.01); *G06F 3/011* (2013.01); *G06K 9/00302* (2013.01); *G06K 9/00832* (2013.01); *B60N 2002/981* (2018.02); *G06F 2203/011* (2013.01)

(56) References Cited

U.S. PATENT DOCUMENTS

| | | | |
|---|---|---|---|
| 9,600,715 B2* | 3/2017 | Natan | G06K 9/00281 |
| 10,475,127 B1* | 11/2019 | Potter | B60R 25/102 |
| 10,950,052 B1* | 3/2021 | Shirley | A61M 21/00 |
| 2016/0217322 A1* | 7/2016 | Kim | G10L 15/063 |

\* cited by examiner

| BIO-SIGNAL | EMOTION FACTOR | Disgust | Anger | Fear | Anxiety | Sadness | Stress | Frustration | Boredom | Neutral | Interest | Distress | Platonic Love | Romantic Love | Pleasure | Joy |
|---|---|---|---|---|---|---|---|---|---|---|---|---|---|---|---|---|
| GSR | | .875 | .775 | .653 | .353 | .545 | | | | .655 | .545 | | | | | .353 |
| EEG | | .555 | 0.864 | .878 | | .545 | | .464 | .477 | .577 | | | | .353 | | |

VEHICLE AND CONTROL METHOD FOR THE SAME

CROSS-REFERENCE TO RELATED APPLICATION(S)

This application claims priority from Korean Patent Application No. 10-2019-0001744, filed on Jan. 7, 2019, the disclosure of which is incorporated herein by reference in its entirety.

BACKGROUND

Technical Field

The present disclosure relates to a vehicle and a control method thereof for operating components of the vehicle based on an emotion of a user in the vehicle.

Description of the Related Art

Recently, a technique for determining an emotional state of a user in a vehicle has been actively studied. Additionally, research on technologies that are able to induce positive emotions of users in the vehicle is being actively conducted. A vehicle produced in the future may provide useful services to vehicle users by determining the emotional state of the user and providing various types of feedback devices capable of reflecting the emotional state of the user.

However, recent technology has merely determined whether the current emotional state of the user in the vehicle is positive or negative, and provides feedback to regulate the output of components in the vehicle based on the determined emotional state of the user in the vehicle.

SUMMARY

It is an aspect of one or more exemplary embodiments to provide a vehicle and a control method thereof capable of determining a positivity of a user in the vehicle, and accumulating a positivity index when the determined positivity is equal to or greater than a predetermined positivity. Additional aspects of the exemplary embodiments will be set forth in part in the description which follows and, in part, will be obvious from the description, or may be learned by practice of the exemplary embodiments.

According to an aspect of an exemplary embodiment, a vehicle may include a bio-signal sensor configured to detect a bio-signal of a user, a display device configured to display an image, and a controller configured to determine at least one of a positivity of the user or change amount of the positivity of the user based on the detected bio-signal, accumulate a positivity index when at least one of the positivity or change amount of the positivity is equal to or greater than a predetermined positivity or a predetermined change amount of the positivity, and transmit a control signal to the display device to display the accumulated positivity index.

The display device may be configured to display a cymatics image which is transformed based on a frequency, and the controller may be configured to determine at least one of a frequency or size of the cymatics image in proportion to the positivity index, and transmit a control signal to the display device to display the cymatics image having at least one of the determined frequency or size. The controller may be configured to transmit a control signal to the display device to display a predetermined image when the positivity index reaches a target positivity index.

The vehicle may further include a feedback device configured to operate to increase the positivity of the user. The controller may be configured to transmit a signal to the feedback device such that the feedback device operates when the positivity index reaches a target positivity index. The feedback device may include vibration elements disposed on a seat of the vehicle, and the controller may be configured to transmit at least one of a control signal such that the vibration elements vibrate at a predetermined frequency or a control signal such that the vibration elements vibrate at a predetermined intensity or more.

The feedback device may include a speaker disposed within the vehicle, and the controller may be configured to transmit a control signal to the speaker to output a predetermined sound. The feedback device may also include a lighting device disposed within the vehicle, and the controller may be configured to transmit at least one of a control signal for the lighting device to emit light at a predetermined frequency, a control signal for the lighting device to emit light at a predetermined brightness, or a control signal for the lighting device to emit light in a predetermined color.

Additionally, the feedback device may include an air-conditioner disposed within the vehicle, and the controller may be configured to transmit at least one of a control signal for the air-conditioner to output a predetermined scent or a control signal for the air-conditioner to output wind of a predetermined mode. The controller may be configured to reset the positivity index to an initial value when the positivity index reaches a target positivity index.

The vehicle may further include a camera configured to obtain image data for the user. The controller may be configured to determine the positivity of the user based on at least one of the image data for the user or the bio-signal of the user. In addition, the vehicle may include an inputter configured to receive information of at least one of an initial value of the positivity index or a cumulative condition of the positivity index. The controller may be configured to transmit the control signal for the display device to display the accumulated positivity index in a form of at least one of a numeral, an emoticon indicating an emotional state, gauge bar, or a letter.

According to an aspect of another exemplary embodiment, a vehicle control method may include detecting a bio-signal of a user, determining at least one of a positivity of the user or change amount of the positivity of the user based on the detected bio-signal, accumulating a positivity index when at least one of the positivity or change amount of the positivity is equal to or greater than a predetermined positivity or a predetermined change amount of the positivity, and displaying the accumulated positivity index.

The vehicle control method may further include determining at least one of a frequency or size of a cymatics image in proportion to the positivity index, and displaying the cymatics image having at least one of the determined frequency or size. In addition, the method may include displaying a predetermined image when the positivity index reaches a target positivity index and transmitting a control signal to operate a feedback device when the positivity index reaches a target positivity index.

The transmitting of the control signal to operate the feedback device when the positivity index reaches the target positivity index may include transmitting at least one of a control signal such that the vibration elements vibrate at a predetermined frequency or a control signal such that the vibration elements vibrate at a predetermined intensity or more. The transmitting of the control signal to operate the feedback device when the positivity index reaches the target positivity index may also include transmitting a control signal for a speaker to output a predetermined sound.

Further, the transmitting of the control signal to operate the feedback device when the positivity index reaches the target positivity index may include transmitting at least one of a control signal for a lighting device to emit light at a predetermined frequency, a control signal for the lighting device to emit light at a predetermined brightness, or a control signal for the lighting device to emit light in a predetermined color. The transmitting of the control signal to operate the feedback device when the positivity index reaches the target positivity index may also include transmitting at least one of a control signal for an air-conditioner to output a predetermined scent or a control signal for the air-conditioner to output wind of a predetermined mode.

BRIEF DESCRIPTION OF THE DRAWINGS

These above and/or other aspects of the disclosure will become apparent and more readily appreciated from the following description of exemplary embodiments, taken in conjunction with the accompanying drawings in which.

DETAILED DESCRIPTION

Figure 1:
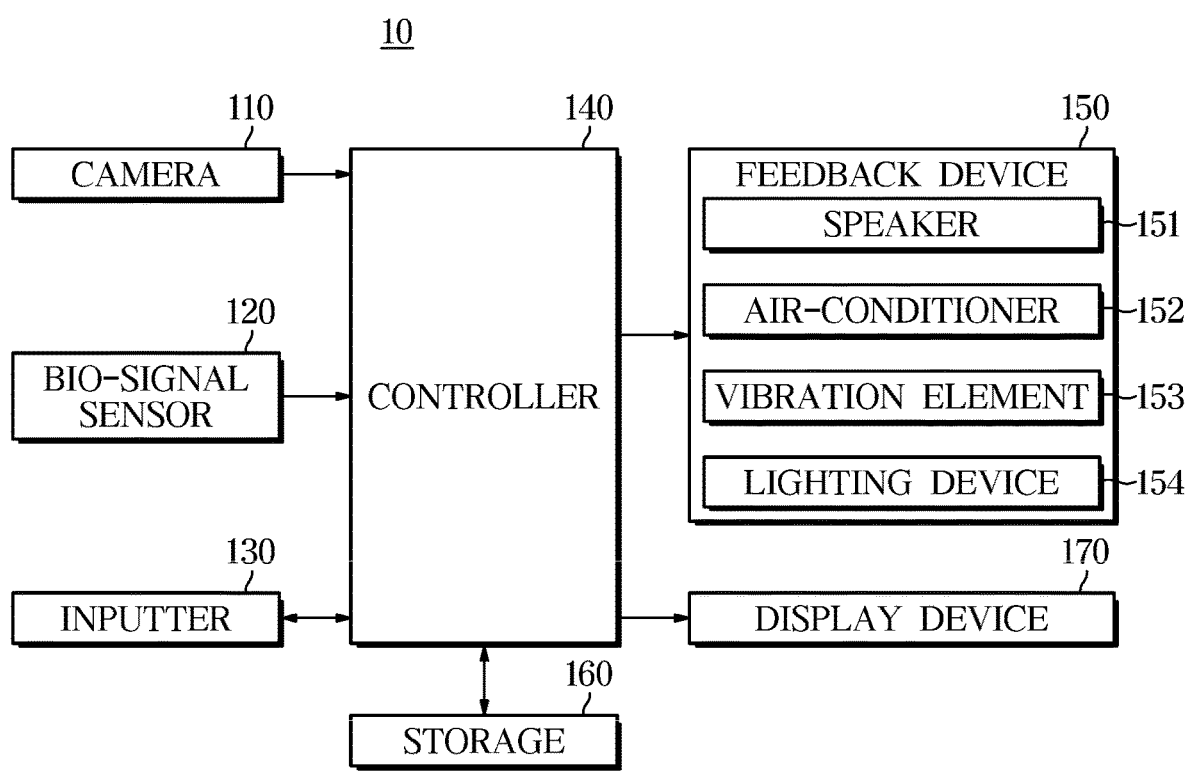
FIG. 1 is a control configuration diagram of a vehicle according to an exemplary embodiment of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing operations described is an example; however, the sequence of and/or operations is not limited to that set forth herein and may be changed as is known in the art, with the exception of operations necessarily occurring in a particular order. In addition, respective descriptions of well-known functions and constructions may be omitted for increased clarity and conciseness.

Additionally, hereinafter, exemplary embodiments will now be described more fully with reference to the accompanying drawings. The exemplary embodiments may, however, be embodied in many different forms and should not be construed as being limited to the embodiments set forth herein. These embodiments are provided so that this disclosure will be thorough and complete and will fully convey the exemplary embodiments to those of ordinary skill in the art. Like numerals denote like elements throughout.

It will be understood that, although the terms first, second, etc. may be used herein to describe various elements, these elements should not be limited by these terms. These terms are only used to distinguish one element from another. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or," includes any and all combinations of one or more of the associated listed items. It will be understood that when an element is referred to as being "connected" or "coupled" to another element, it can be directly connected or coupled to the other element or intervening elements may be present.

In contrast, when an element is referred to as being "directly connected" or "directly coupled" to another element, there are no intervening elements present. The terminology used herein is for the purpose of describing particular embodiments only and is not intended to be limiting. As used herein, the singular forms "a," "an," and "the" are intended to include the plural forms as well, unless the context clearly indicates otherwise.

Reference will now be made in detail to the exemplary embodiments of the present disclosure, examples of which are illustrated in the accompanying drawings, wherein like reference numerals refer to like elements throughout.

FIG. 1 is a control configuration diagram of a vehicle according to an exemplary embodiment of the present disclosure. Referring to FIG. 1, a vehicle 10 according to an exemplary embodiment may include a camera 110 configured to obtain image data for a user in the vehicle 10, a bio-signal sensor 120 configured to detect a bio-signal of the user, an inputter 130 configured to receive an input from the user, a controller 140 configured to determine at least one of a positivity of the user or change amount of the positivity of the user based on the detected bio-signal, accumulate a positivity index when at least one of the positivity or change amount of the positivity is equal to or greater than a predetermined positivity or a predetermined change amount of the positivity, and transmit a control signal to a display device 170 to display the accumulated positivity index, a feedback device 150 disposed within the vehicle 10 for operating to increase the positivity of the user under the control signal of the controller 140, a storage 160 configured to store various types of information necessary for operating the vehicle 10, and the display device 170 configured to display various images.

Particularly, the camera 110 according to one exemplary embodiment may be configured to capture the user in the vehicle 10 and obtain the image data for the user. The image data for the user may include information on a facial expression of the user, that is, the motion of a facial composition. The camera 110 may include a plurality of lenses and an image sensor. The image sensor may include a plurality of photodiodes for converting light into electrical signals, and the plurality of photodiodes may be arranged in a two-dimensional matrix.

In addition, the camera 110 may be provided as the infrared camera to capture the user at night driving. The image data for the user may include information regarding the facial expression of the user. The camera 110 may be installed at a position such as a dashboard, a windshield, or a seat of the vehicle 10, and there is no limitation on the installation position and number. Since the image data for the user obtained by the camera 110 may be used by the controller 140 to identify the facial expression of the user and the position of the user, the camera 110 may be installed at the front position of the user.

The user may include both a driver and a passenger of the vehicle 10, and the camera 110 may be configured to obtain the image data for all of the users located within the vehicle 10. In addition, the bio-signal sensor 120 according to one exemplary embodiment may be configured to detect the bio-signals of each of the users in the vehicle 10. The detected bio-signals of the users may be transmitted to the controller 140 and/or stored in the storage 160. The bio-signal sensor 120 may be installed at various positions in the vehicle 10. For example, the bio-signal sensor 120 may be disposed on the seat, a seat belt, a steering wheel, and a handle provided on a door. The bio-signal sensor 120 may be provided as a type of wearable device that may be worn by the user.

The bio-signal sensor 120 may include a galvanic skin response (GSR) sensor configured to detect the skin electrical conductivity of the user, a skin temperature sensor configured to detect the skin temperature of the user, a heart rate (HR) sensor configured to detect a heart rate, an electroencephalogram (EEG) sensor configured to detect the user's brain waves, a speech recognition sensor configured to detect the user's voice signal, a blood pressure detecting sensor configured to detect the user's blood pressure, and an eye tracker capable of tracking the position of the pupils of the user. The sensors included in the bio-signal sensor 120 are not limited to the above sensors, and may include all sensors capable of detecting or collecting human bio-signals.

The inputter 130 according to one exemplary embodiment may be configured to receive input from the user. Specifically, the inputter 130 may be configured to receive an input, such as an input for an operation of the feedback device 150 (e.g., a predetermined sound, a predetermined scent, etc.), an input for an initial value of the positivity index, and an input for cumulative conditions and the like, from the user. For the above purpose, the inputter 130 may be disposed in a center fascia installed at the center of the dashboard, and may be implemented using a physical button, a knob, a touch pad, a touch screen, a stick type operation device, or a trackball.

In particular, the inputter 130 provided on the touch screen may be provided on the display device 170 within the vehicle 10. However, the position and the manner of implementation of the inputter 130 are not limited to the above-described example, and may be included without limitation as long as the position and the implementation manner of the input of the user may be received.

The controller 140 according to an exemplary embodiment may be configured to determine at least one of the positivity of the user or change amount of the positivity of the user based on at least one of the detected bio-signal or obtained image data for the user, accumulate a positivity index when at least one of the positivity or change amount of the positivity is equal to or greater than a predetermined positivity or a predetermined change amount of the positivity, and transmit the control signal to the display device 170 to display the accumulated positivity index.

In other words, the positivity index does not mean the current positivity of the user, but may be determined as an accumulated index when at least one of the positivity or change amount of the positivity is equal to or greater than a predetermined positivity or predetermined change amount of the positivity. Specifically, the controller 140 may be configured to determine the facial expression of the user based on the image data for the user, and obtain information regarding an emotional state that corresponds to the determined facial expression. The method for obtaining information regarding the emotional state of the user based on the image data will be described in detail later.

In addition, the controller 140 may be configured to obtain information regarding a corresponding emotional state based on the user's bio-signals. The method for obtaining information on the emotional state of the user based on the bio-signals will be described later in detail. The predetermined positivity may be determined to detect that the user is pleased when the positivity of the user is equal to or greater than the predetermined positivity. The predetermined change amount of the positivity may also be determined to detect that the user is pleased when the change amount of the positivity of the user is equal to or greater than the predetermined change amount of the positivity. The predetermined positivity and/or the predetermined change amount of the positivity may be stored in the storage 160 and may be determined by the controller 140 based on the number and characteristics of the users and by input from the user through the inputter 130.

In addition, the controller 140 may be configured to accumulate the positivity index when at least one of the positivity or change amount of the positivity is equal to or greater than a predetermined positivity or a predetermined change amount of the positivity. The positivity index, as an index which is accumulated when the positivity of the user is equal to or greater than the predetermined positivity, or when the change amount of the positivity of the user is equal to or greater than the predetermined change amount of the positivity, is an index which is accumulated when the user feels pleasure. The degree of the accumulation of the positivity index may depend on various factors such as how greater the positivity of the user than the predetermined positivity, how greater the change amount of the positivity of the user than the predetermined change amount of the positivity, and how long that state is maintained.

For example, the positivity index may be accumulated based on the degree of the user's positivity changing within a unit time. In other words, if the amount of the positivity change of the user is equal to or greater than a predetermined change amount, the positivity index may be accumulated. In particular, even if the positivity of the user is less than a predetermined positivity, the positivity index may be accumulated since the change amount of the positivity is greater than a predetermined change amount.

Additionally, the user may include not only the driver but also the passengers, and if the average positivity of the driver and the passengers is greater than a predetermined positivity, the positive index may be accumulated. Particularly, a weight may be allocated to the positivity of the driver when the average value is calculated, so that the positivity of the driver has the greatest influence. However, the weighted object is not limited to the driver but may be the passenger by the input from the user through the inputter 130.

Information of at least one of an initial value of the positivity index or a cumulative condition of the positivity index may be input through the inputter 130 from the user. The controller 140 may be configured to determine at least one of a frequency or size of a cymatics image in proportion to the positivity index, and transmit a control signal to the display device 170 to display the cymatics image having at least one of the determined frequency or size.

In particular, the controller 140 according to an exemplary embodiment may be configured to determine at least one of the frequency or size of the cymatics image in proportion to the positivity index as the positivity index is accumulated and increased, and transmit the control signal to the display device 170 to display the cymatics image having at least one of the determined frequency or size. In response to determining at least one of the frequency or size of the cymatics image in proportion to the positivity index, the controller 140 may access a look-up table and/or an algorithm including a formula for determining the frequency and size stored in the storage 160, and/or input from the user received from the inputter 130.

The controller 140 according to an exemplary embodiment may be configured to transmit a control signal to the display device 170 to display a predetermined image when the positivity index reaches a target positivity index. Additionally, the controller 140 may be configured to directly transmit the control signal to the display device 170 to display a predetermined image regardless of the accumulated positivity index if the positivity of the user is greater than a threshold which is greater than the predetermined positivity, or the change amount of the positivity of the user is greater than a threshold which is greater than the predetermined change amount.

The predetermined image may be an image of a color that increases an emotion factor that corresponds to the positivity. The color that increases the emotion factor corresponding to the positivity may be determined at a design stage, determined by the controller 140 based on correlation information between the color and the emotion factor received from a server, or determined by the user through the inputter 130. The predetermined image may include any images that increase the emotion factor corresponding to the positivity. For example, the predetermined image may include a graphic element such as bursting fireworks, may include a plurality of the cymatics images, or may include images determined by the user through the inputter 130.

The target positivity index, as a predetermined positivity index, may be determined to reward the user when the positive index of the user reaches the target positivity index. For example, the positivity index when the number of times that the positivity and/or the change amount of the positivity becomes equal to or greater than the predetermined positivity and/or the predetermined change amount is 100 may be determined as the target positivity index. Without any limitation, the target positivity may be determined according to the conditions for calculating the positivity index and/or characteristics of the user and/or may be determined by the users through the inputter 130.

The controller 140 may be configured to transmit a signal to the feedback device 150 to operate when the positivity index reaches the target positivity index. Of course, the controller 140 may be configured to directly transmit the control signal to the feedback device 150 to operate regardless of the accumulated positivity index if the positivity of the user is greater than a threshold which is greater than the predetermined positivity, or the change amount of the positivity of the user is greater than a threshold which is greater than the predetermined change amount.

In particular, the controller 140 may be configured to execute an operation on the determined current emotional state through a neural network, and generate a control signal for determining the operation of the feedback device 150 based on the information on performing of the operation through the neural network. The operation of the feedback device 150 may include various operations based on the type of the feedback device 150. The information on performing of the operation through the neural network may include information regarding a predetermined frequency and/or a predetermined intensity at which vibration elements 153 vibrate, a predetermined sound and/or predetermined loudness level at which a speaker 151 outputs a noise, a predetermined frequency, brightness and/or color at which a lighting device emits, and/or a predetermined scent and/or wind of the predetermined mode at which an air-conditioner 152 outputs.

The neural network refers to machine learning that forms a neural structure capable of performing deep learning of which the weight and bias corresponding to the configuration of the neural network continuously change to increase reliability. Specifically, the vehicle 10 continuously updates the weight, bias, and activation function to increase the result of inference of the neural network based on the information regarding the positivity of the user, the positivity index, the target positivity index, and/or the increased amount of the positivity of the user according to an operation of the feedback device 150. In other words, the vehicle 10 may be configured to store information regarding the determined operation and increased amount of the positivity of the user while driving, to thus update the neural network continuously based on the stored information.

The neural network may be stored in the storage 160 in the form of a computer program. Hereinafter, the computation performed by the neural network in the coding form of the computer program will be described. However, the neural network is not limited to the stored computer program. The neural network may include a convolution neural network (CNN) for generating a feature map output by convoluting a current emotional state and a target emotional state, and inputting the feature map to a neural network, and may be performed with other deep-running algorithms including recurrent neural networks (RNN).

Accordingly, the vehicle 10 may be configured to determine the most suitable operation pattern of the feedback device 150 based on the current emotional state and the target emotional state through the neural network that is continuously updated while driving. In other words, the controller 140 may be configured to determine the type of operation and the operation time of the feedback device 150 capable of maximizing the user's positivity based on the current positivity and/or increased amount of the positivity.

The controller 140 may be configured to transmit a signal to the feedback device 150 to operate when the positivity index reaches a target positivity index. Operation of the feedback device 150 will be described later in detail. In addition, the controller 140 may be configured to transmit the control signal to the display device 170 to display the accumulated positivity index in a form of at least one of a numeral, an emoticon indicating an emotional state, gauge bar, or a letter, and this will be described in detail later with reference to FIGS. 5A to 5C.

The feedback device 150 may include at least one of the speaker 151, the air-conditioner 152, the vibration element 153, and a lighting device 154, and may be configured to operate to increase the positivity of the user. The operation of each of the feedback devices 150 and transmission of a control signal of the controller 140 will be described later in detail with reference to FIGS. 6 and 7.

Further, the controller 140 may be configured to reset the positivity index to the initial value when the positivity index reaches the target positivity index. Specifically, when the positivity index reaches the target positivity index, the feedback device 150 may be configured to output a reward to the user and the controller 140 may be configured to reset the accumulated positive index to the initial value, thereby inducing the user to accumulate the positivity index again. The initial value may include the case where the positivity index is 0, but it may be determined by the user's setting through the inputter 130.

The storage 160 according to one exemplary embodiment may be configured to store various types of information necessary for operating the vehicle 10. For example, the storage 160 may be configured to store image data obtained by the camera 110, bio-signals of the user detected by the bio-signal sensor 120, correlation information between the bio-signals of the user and the emotion factors, information regarding the emotional state of the user, emotion model, and information on the neural network. The data stored in the storage 160 may be transmitted to the controller 140.

The storage 160 may be implemented as a non-volatile memory such as a cache, ROM, programmable ROM, EPROM, EEPROM, and a flash memory; a volatile memory such as random access memory (RAM); or a storage medium such as a hard disk drive (HDD) and a CD-ROM to store various types of information, but is not limited thereto. The storage 160 may be a memory implemented as a separate chip or may be implemented as a single chip with a processor corresponding to the controller 140.

The display device 170 according to one exemplary embodiment may be disposed within the vehicle 10 and may be configured to display various images such as a positivity index image, a cymatics image transformed according to a frequency, a predetermined image, etc., in accordance with a control signal of the controller 140. The display device 170 will be described in detail later with reference to FIGS. 5A to 5C.

Figure 2:
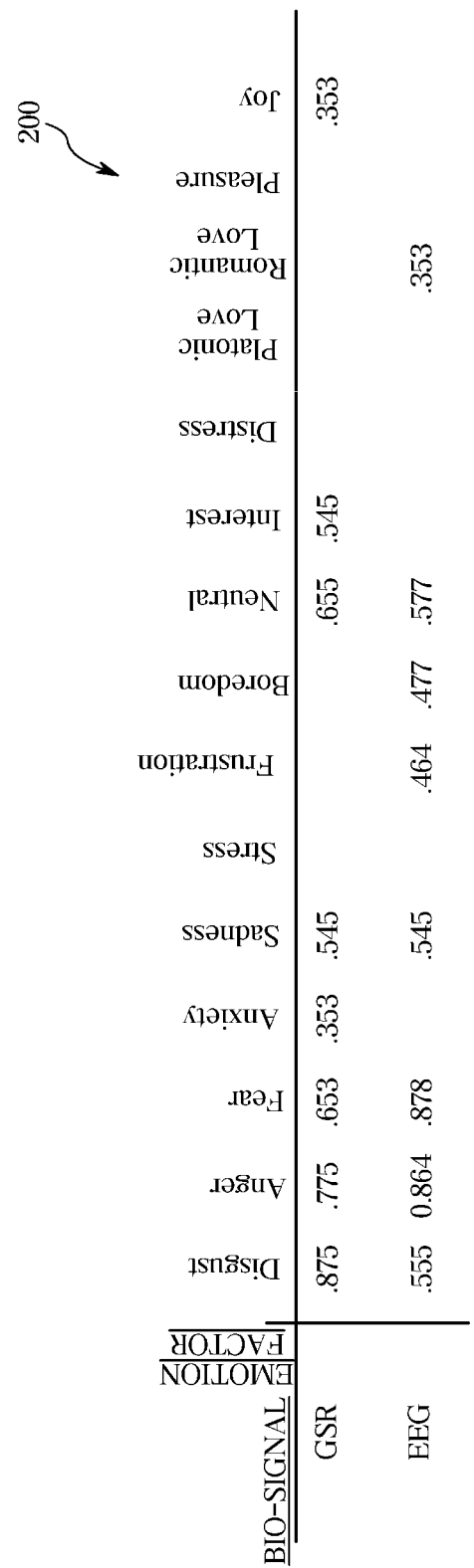
FIG. 2 is a diagram illustrating correlation information between a bio-signal and an emotion factor according to an exemplary embodiment of the present disclosure.
Figure 3:
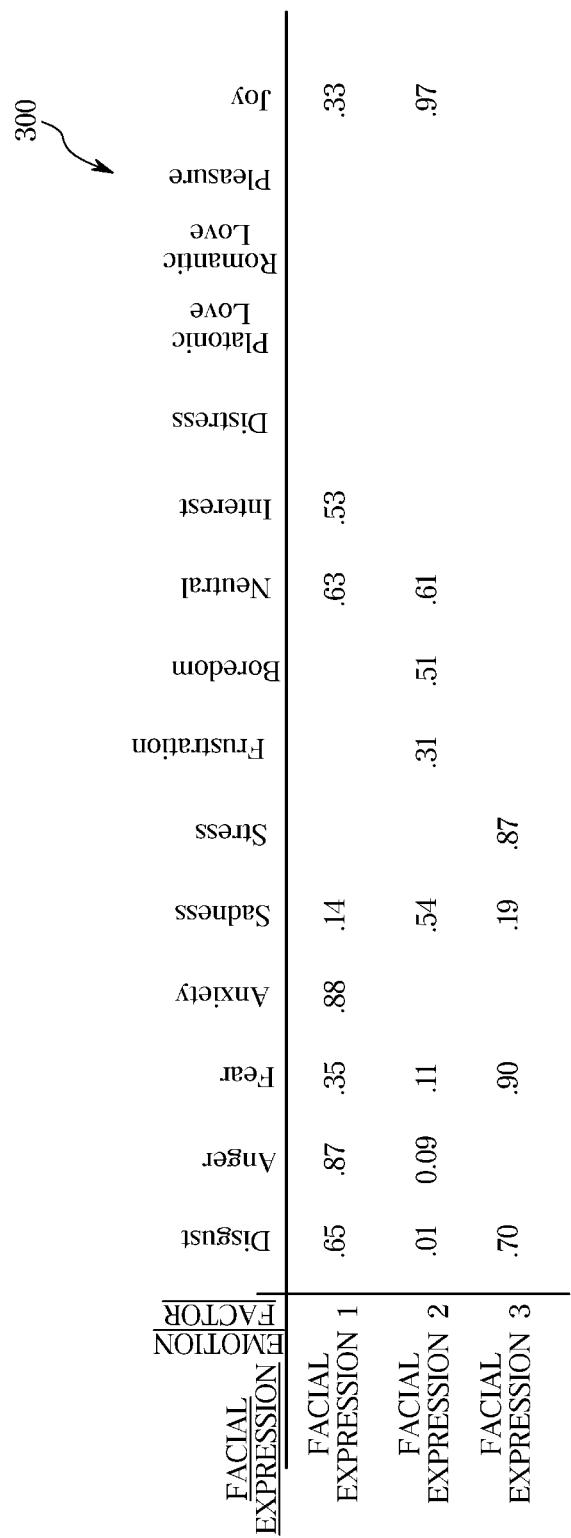
FIG. 3 is a diagram illustrating correlation information between a facial expression and an emotion factor according to an exemplary embodiment of the present disclosure.
Figure 4:
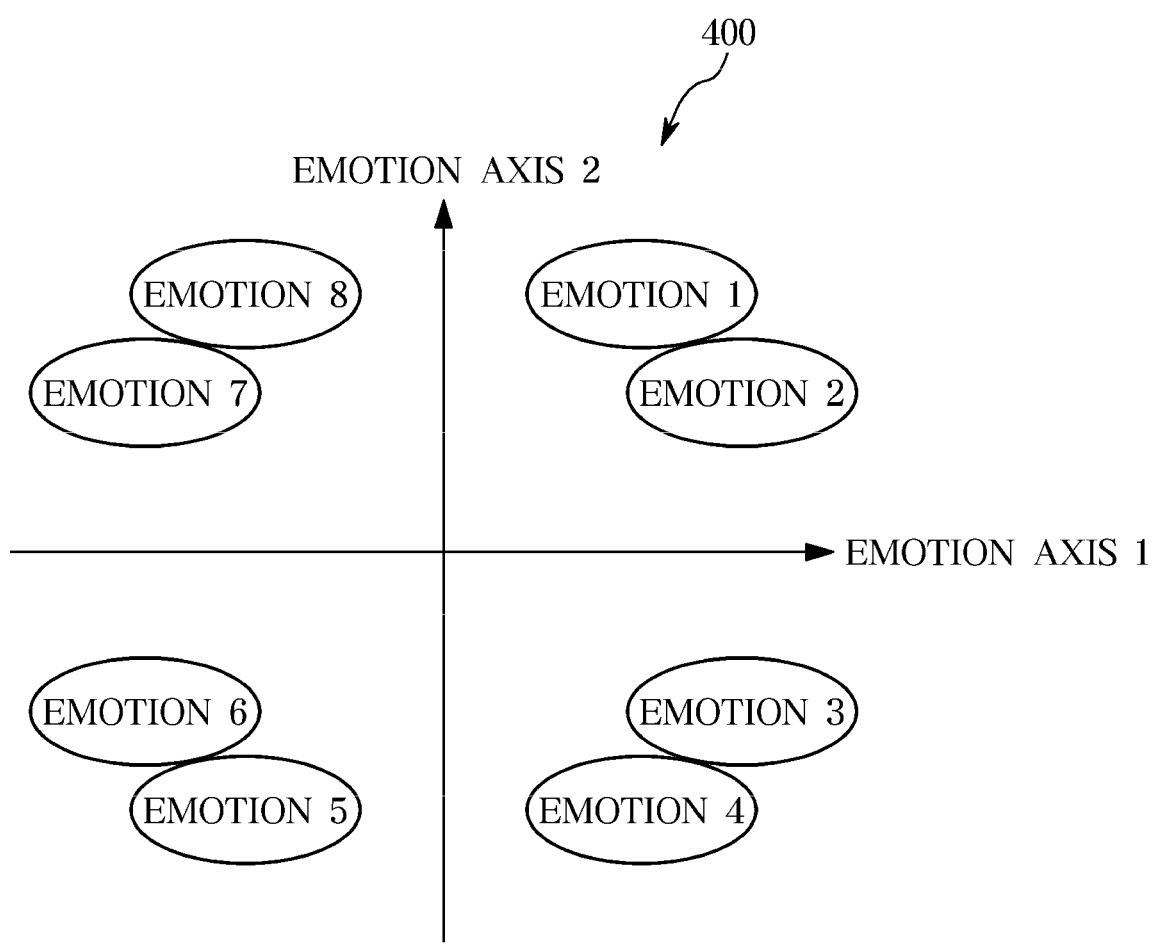
FIG. 4 is a diagram illustrating an emotion model according to an exemplary embodiment of the present disclosure.

Hereinafter, the vehicle 10 obtaining the information regarding the emotional state of the user based on the image data obtained by the camera 110 and/or the bio-signals detected by the bio-signal sensor 120 will be described in detail with reference to FIGS. 2 to 4. FIG. 2 is a diagram illustrating correlation information between a bio-signal and an emotion factor according to an exemplary embodiment of the present disclosure, FIG. 3 is a diagram illustrating correlation information between a facial expression and an emotion factor according to an exemplary embodiment of the present disclosure, and FIG. 4 is a diagram illustrating an emotion model according to an exemplary embodiment of the present disclosure.

Referring to FIG. 2, correlation information 200 between the bio-signals and the emotion factors according to an exemplary embodiment may include correlation information between an electro skin reaction (GSR), an EEG and an emotion factor. As described in FIG. 2, a GSR signal has a correlation value of 0.875 and 0.775 with emotion factors of Disgust and Anger, respectively, and thus, the GSR signal has a high correlation with the emotion factors of Disgust and Anger. Accordingly, the bio-signals detected by the GSR sensor may be the basis on which the emotion of the user is determined as Disgust or Anger.

In the case of an emotion factor of Joy, the correlation value with the GSR signal is relatively low (0.353), and thus, the GSR signal has a low correlation with the emotion factor of Joy. An EEG signal has a correlation value of 0.864 and 0.878 with emotion factors of Anger and Fear, respectively, which indicates that the EEG signal has a high correlation with the emotion factors of Anger and Fear. Thus, the bio-signals detected by the EEG sensor may be the basis on which the emotion of the user is determined as Anger or Fear.

As described above, the controller 140 may be configured to obtain information regarding the emotional state of each of the users using the correlation information 200 between the bio-signals and the emotion factors. Since the information shown in FIG. 2 is only a result of experiments, it may vary based on the experimental environment. Additionally, even if FIG. 2 describes the correlation information between the GSR and the EEG and emotion factors, the correlation information 200 between the bio-signals and the emotion factors may vary with different types of the bio-signals detected by the bio-signal sensor 120 mounted within the vehicle 10.

Referring to FIG. 3, the controller 140 may be configured to determine the facial expressions of each of the users shown in the images of the users captured by the camera 110, and apply a Facial Action Coding System (FACS) to the facial expressions of each of the users to obtain information regarding the emotional state of each of the users. Specifically, the controller 140 may be configured to extract feature points from the face of the user, and extract a plurality of facial elements using the extracted feature points.

The plurality of facial elements may include eyebrows, eyes, nose, mouth, and the like. The controller 140 may be configured to combine the patterns of the extracted plurality of facial elements and compare the combined pattern with correlation information 300 between the facial expressions and the emotion factors stored in the storage 160. The correlation information 300 between the facial expressions and the emotion factors corresponds to the information indicating the relationships between the facial expressions and the emotion factors.

Additionally, the controller 140 may be configured to determine the facial expression that corresponds to the same pattern or the most similar pattern to the combined pattern of the user among the correlation information 300 between the facial expressions and the emotion factors as the facial expression of the user. The controller 140 may be configured to obtain information regarding the emotional state indicating the emotional state of the user based on a correlation value in the correlation information 300 between the determined facial expression of the user and the emotion factor.

For example, when the determined facial expression of the user corresponds to a facial expression 2 in the correlation information 300 between the facial expressions and the emotion factors, the controller 140 may be configured to determine that the emotion factor Joy, which has the highest correlation value, is the emotional state of the user. The correlation information 300 between the facial expressions and the emotion factors described in FIG. 3 only includes a facial expression 1, the facial expression 2 and a facial expression 3, but may include any facial expression capable of classifying the emotions of the user. Accordingly, the controller 140 be configured to analyze the internal image of the vehicle 10 captured by the camera 110 to determine the facial expressions of the respective users in the vehicle 10, and based on the determined facial expressions, information about the emotional state may be obtained.

Referring to FIG. 4, an emotion model 400 classifies emotions of the user, which are indicated according to at least one of the image data and the bio-signals of the user, on a graph. The emotion model 400 classifies the emotions of the user based on a preset emotion axis. The emotion axis may be determined based on the emotions of the user determined by the image data of the user or the bio-signals of the user. For example, emotion axis 1 may be degrees of positivity or negativity, measurable by the voice of the user or the facial expressions of the user, and emotion axis 2 may be degrees of excitability or activity measurable by the GSR or the EEG.

If the emotion of the user has high degrees of positivity and high degrees of excitability, the emotion may be classified as Emotion 1 or Emotion 2. Conversely, if the emotion of the user has negative (−) excitability, that is, the user has high degrees of excitability with negativity, the emotion may be classified as Emotion 3 or Emotion 4. This emotion model may be a Russell's emotion model. The Russell's emotion model is represented by a two-dimensional graph based on the x and y axes, with Joy (0 degrees), Excitement (45 degrees), Arousal (90 degrees), Pain (135 degrees), Unpleasantness (180 degrees), Depression (225 degrees), Sleepiness (270 degrees), and Relaxation (315 degrees). In addition, the eight areas are divided into 28 emotions and classified into 8 emotions.

Accordingly, the controller 140 may be configured to obtain information regarding the emotional state of each of the users by using the facial expressions and the bio-signals of each of the users, the correlation information 200 between the emotion factors and the bio-signals, the correlation information 300 between the facial expressions and the emotion factors, and the emotion model 400. The obtained information regarding the emotional state may be defined as a numerical value for each of positivity and excitability based on the degree of the emotion. Specifically, each of the positivity and the excitability may be expressed numerically as a value between −100 and 100 according to the degree. However, the numerical value according to the degree is merely an example, and may be any numerical value without limitation as long as it corresponds to a numerical value that represents the degree of emotion.

Figure 5A:
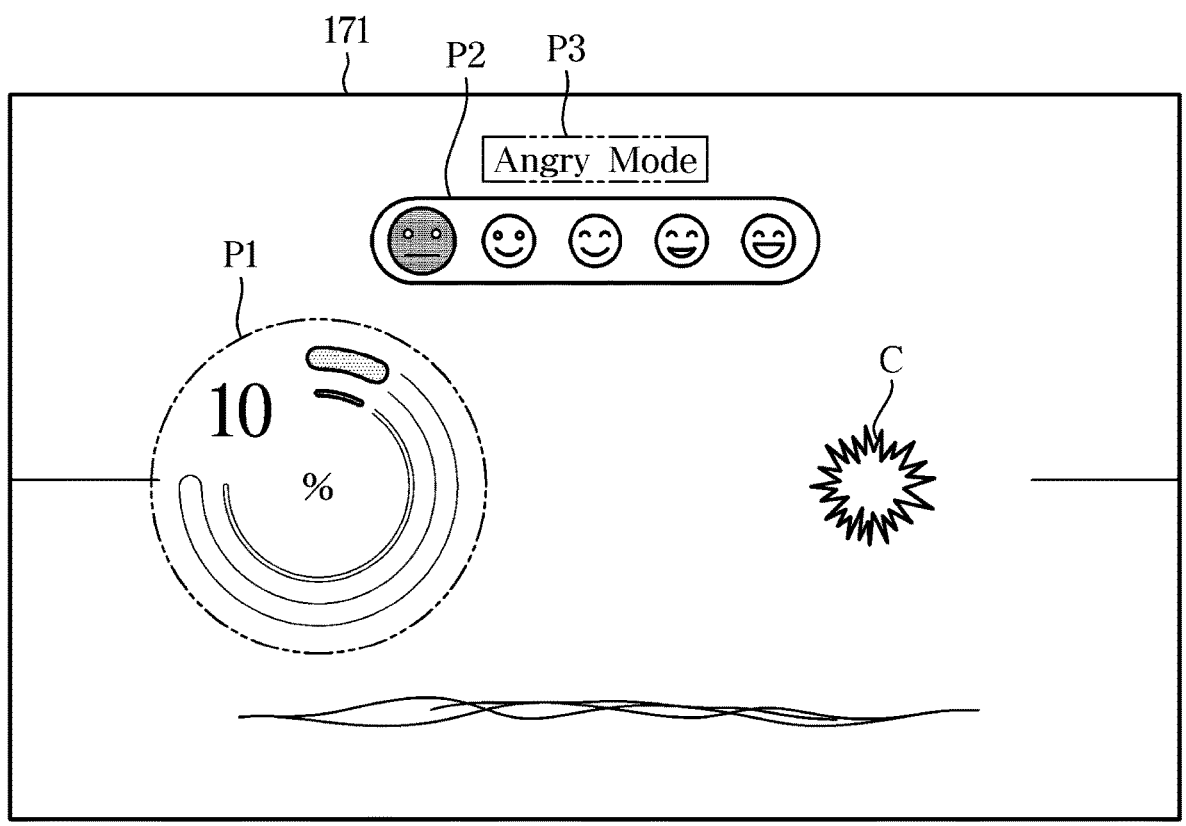
FIG. 5A to FIG. 5C are diagrams illustrating a displayed image of a vehicle according to an exemplary embodiment of the present disclosure.
Figure 5B:
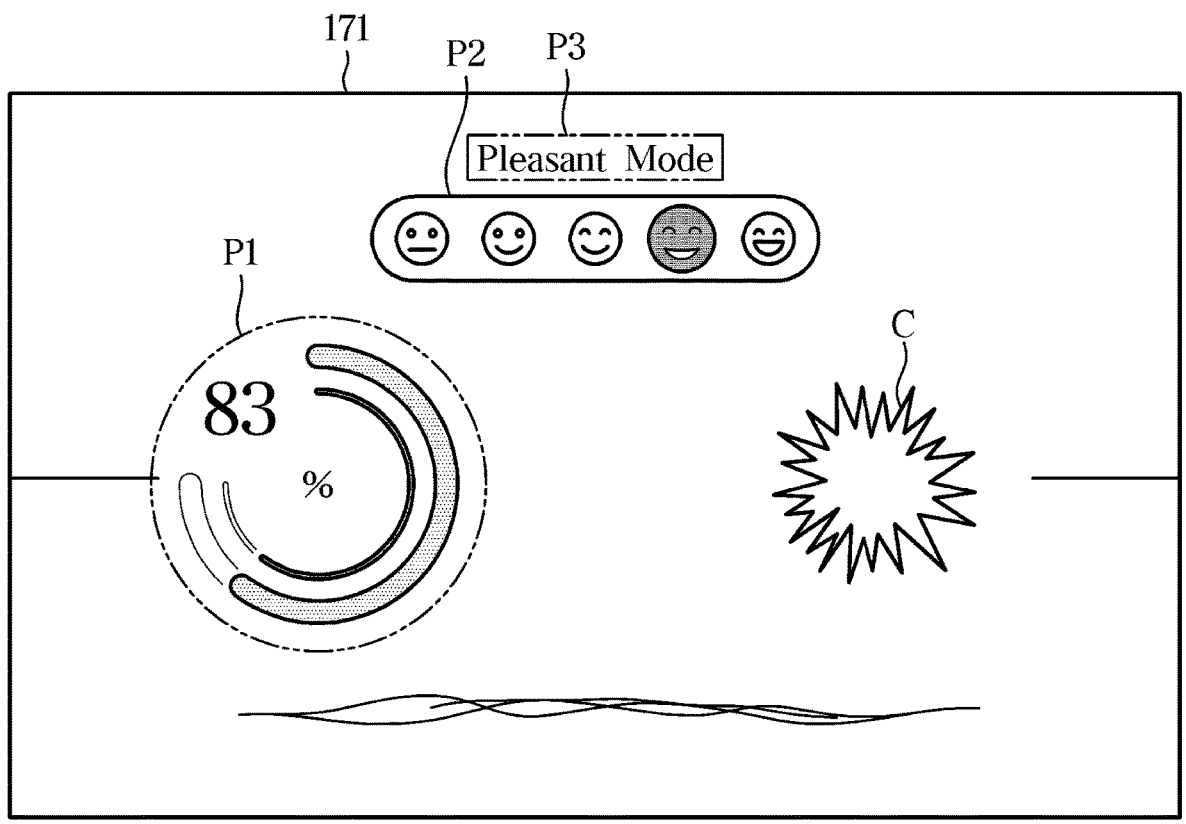
Figure 5C:
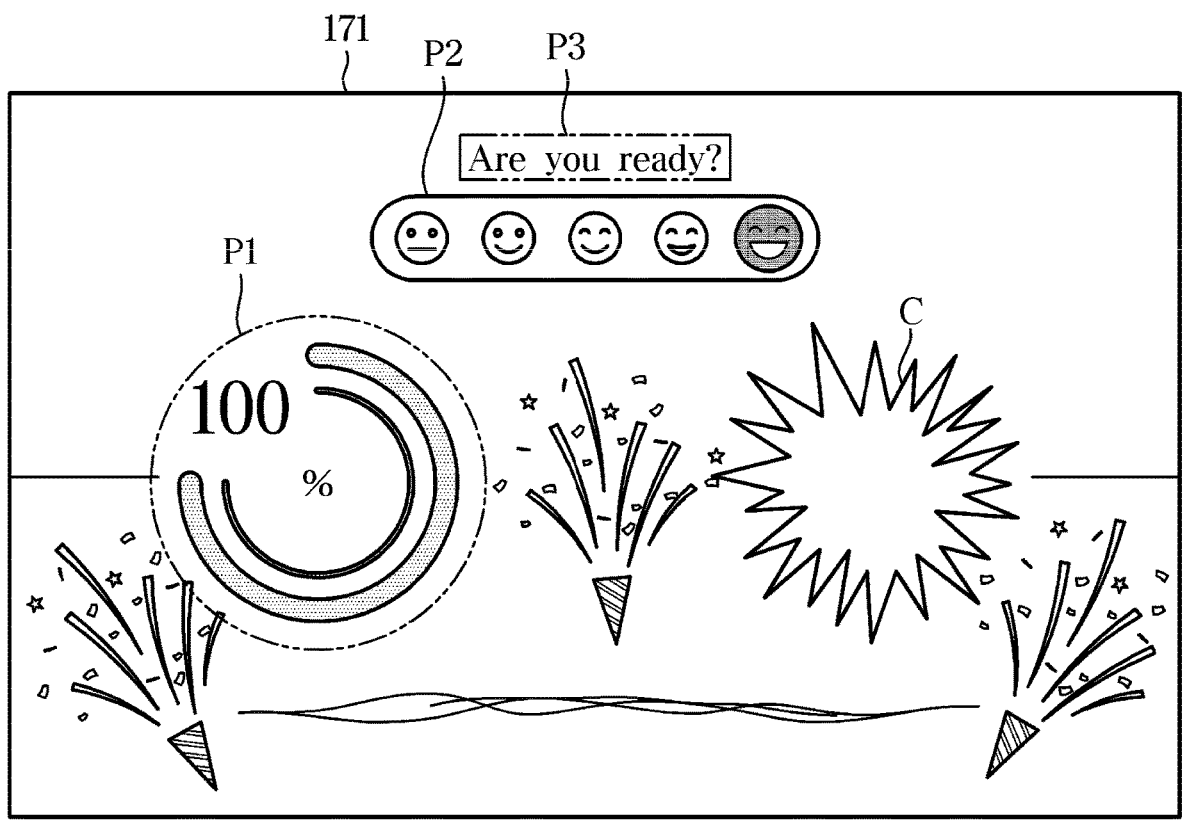

Hereinafter, an aspect in which the vehicle 10 according to the exemplary embodiment operates the display device 170 will be described in detail with reference to FIGS. 5A and 5B. FIGS. 5A to 5C are diagrams illustrating a displayed image of a vehicle according to an exemplary embodiment of the present disclosure.

Particularly, the display device 170 may be mounted inside the vehicle 10 and may include a panel. For example, the display device 170 may be disposed in a cluster, across the cluster and the center fascia, and on a ceiling inside the vehicle 10. The panel may be a cathode ray tube (CRT) panel, a liquid crystal display (LCD) panel, a light emitting diode (LED) panel, an organic light emitting diode (OLED) panel, a plasma display panel (PDP), or a field emission display (FED) panel. The location and number of the display device 170 has no limitation as long as the display device 170 may be visually communicate to the user of the vehicle 10.

The display device 170 according to one exemplary embodiment may be configured to display an accumulated positivity index according to the control signal of the controller 140. Specifically, in accordance with the control signal of the controller 140, the positivity index may be displayed in the form of at least one of a numeral P1, an emoticon P2 indicating the emotional state, a gauge bar P1, and a letter P3. When the positivity index is displayed in the form of the numeral P1, there is no limitation on how the form of the numeral P1 displayed, and therefore, the absolute numeral value P1 may be displayed. However, for comparison with the target positivity index, a percentage (%) numeral value may be preferred.

The target positivity index may be 100(%), but is not limited thereto and may be set differently as described above. When the positivity index is displayed in the form of the emoticon P2 indicating the emotional state, the degree of the positivity index may be displayed according to the expression of the emoticon, but the present invention is not limited to the expression, and various modifications are possible. For example, the user may know that the positivity index is low when the emoticon P2 of an angry expression is displayed, and the positivity index is high when the emoticon P2 of a pleasant expression is displayed.

When an affirmative exponent is displayed in the form of the gauge bar P1, the gauge bar P1 may be in the form of a rod, or may be round as shown in FIGS. 5A to 5C, but the shape of the gauge bar is not limited to. The gauge bar P1 may be based on the target positivity index and a filled portion in the gauge bar may represent the value of the current positivity index of the user to allow the user to intuitively determine how much positivity index should be accumulated up to the target positivity index. When the positivity index is displayed in the form of the letter P3, the positivity index may be represented with characters with meanings such as "Angry" (P3), "Pleasant" (P3), and "Are you ready?" (P3), however, letters such as "A," "B," and "C" may be used instead of the type of the characters. In other words, the kind type letter is not limited.

Referring to FIG. 5A, the display device 170 may be configured to display the positivity index as the gauge bar P1 in which the positive index is fulfilled about 10(%), as the numeral P1 (10%), as the emoticon P2 of an angry expression, and as characters "Angry" P3. Referring to FIG. 5B, the display device 170 may be configured to display the positivity index as the gauge bar P1 in which the positive index is fulfilled about 83(%), as the numeral P1 (83%), as the emoticon P2 of a pleasant expression and as characters "Pleasant" P3. Referring to FIG. 5C, the display device 170 may be configured to display the positivity index as the gauge bar P1 in which the positive index is fulfilled about 100(%), as the numeral P1 (100%), as the emoticon P2 of a very pleasant expression and as characters "Are you ready?" P3.

Additionally, the display device 170 may be configured to display a cymatics image C which is transformed according to a frequency, and the controller may be configured to determine at least one of a frequency or size of the cymatics image C in proportion to the positivity index, and transmit a control signal to the display device 170 to display the cymatics image C having at least one of the determined frequency or size. The cymatics image C refers to an image in which the frequency and shape of the signal of a sound are displayed on the display device 170 in a 2D image, and may be associated with the sound of the speaker 151 installed within the vehicle 10. The controller 140 may be configured to determine at least one of the frequency or size of the cymatics image C in proportion to the positivity index, and access the look-up table and/or the algorithm including a formula for determining the frequency and size stored in the storage 160, and/or input from the user received from the inputter 130.

Referring to FIGS. 5A to 5C, the size of the cymatics image C gradually increases according to the accumulated positivity index of the user. Although not shown in detail in FIGS. 5A to 5C, not only the frequency and size of the cymatics image C may be changed, but also the color, shape, number, etc. may be changed. The change in the cymatics image C may include all changes that may be correlated with and interact with the user's positive index. The display device 170 according to an exemplary embodiment may be configured to display a predetermined image when the positivity index reaches a target positivity index according to the control signal of the controller 140.

Referring to FIG. 5C, an image displayed may be on the display device 170 when the positivity index reaches the target positivity index. At this time, the display device 170 may be configured to display the predetermined image according to the control signal of the controller 140. The predetermined image may be an image of a color that increases the emotion factor corresponding to the positivity. The color that increases the emotion factor that corresponds to the positivity may be determined at the design stage, determined by the controller 140 based on a correlation information between the color and the emotion factor received from a server, or determined by the user through the inputter 130.

The predetermined image may include any images increasing the emotion factor corresponding to the positivity. For example, the predetermined image may include a graphic element such as bursting fireworks, may include a plurality of the cymatics images C, or may include the images determine by the user through the inputter 130. Referring to FIG. 5C, the display device 170 may be configured to display the image of bursting fireworks according to the control signal of the controller 140.

Although not shown in the drawing, the controller 140 may be configured to stop transmitting the control signal for the display device 170 to display the positivity index, and transmit only the control signal for the display device 170 to display the predetermined image to maximize the increase of positivity of the users by utilizing all parts of the display device 170.

Figure 6:
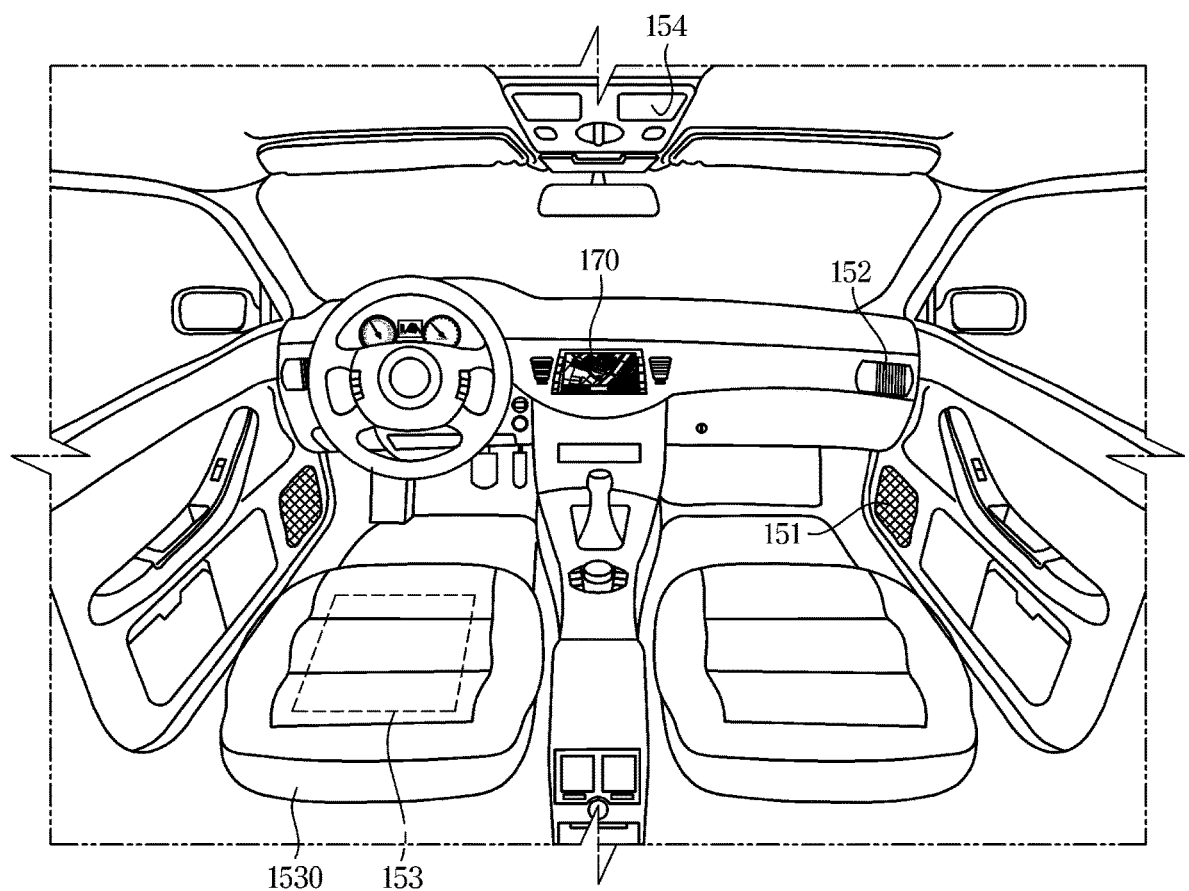
FIG. 6 is a diagram illustrating a feedback device in a vehicle according to an exemplary embodiment of the present disclosure.
Figure 7:
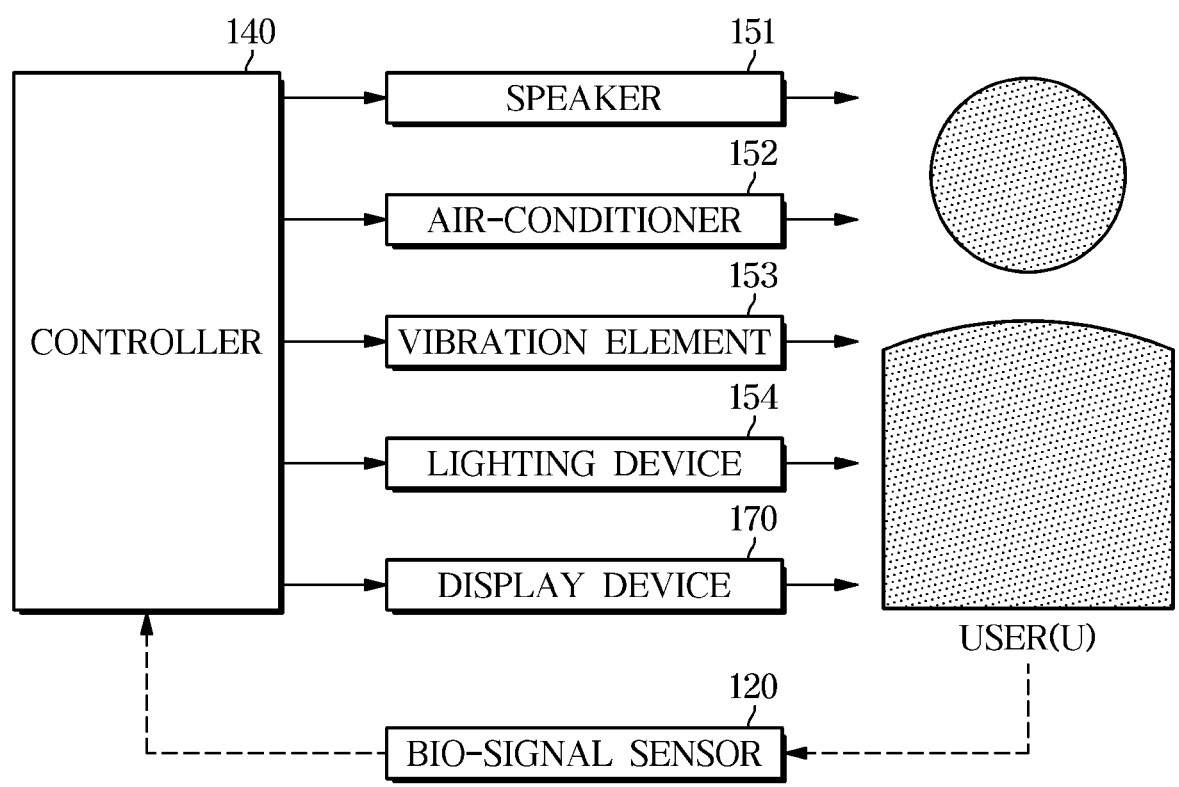
FIG. 7 is a diagram illustrating feedback control of a vehicle according to an exemplary embodiment of the present disclosure.

Hereinafter, the manner in which the vehicle 10 according to the exemplary embodiment controls the feedback device 150 will be described in detail with reference to FIGS. 6 and 7. FIG. 6 is a diagram illustrating a feedback device in a vehicle according to an exemplary embodiment of the present disclosure and FIG. 7 is a diagram illustrating feedback control of a vehicle according to an exemplary embodiment of the present disclosure. The feedback device 150 may include at least one of the speaker 151, the air-conditioner 152, the vibration element 153 and the lighting device 154, and may be operable to increase the positivity of the user.

Referring to FIG. 6, the speaker 151 according to one exemplary embodiment may be configured to output a predetermined sound according to a control signal of the controller 140. Additionally, the speaker 151 may be disposed within the vehicle 10 and may be provided without any locational limitation as long as it is a position where the sound output by the speaker 151 is capable of being heard by the user of the vehicle 10.

The air-conditioner 152 according to one exemplary embodiment may be configured to output a predetermined scent or output a wind of a predetermined mode according to a control signal of the controller 140. The air-conditioner 152 may be mounted within the vehicle 10 to blow wind (e.g., warm or cool air) into the interior space of the vehicle 10 under the operation of the controller 140. Specifically, the air-conditioner 152 may include a compressor, a condenser, an expansion valve, and a heat exchanger, wherein the compressor, the condenser, the expansion valve, and the heat exchanger may be connected through at least one refrigerant passage. The refrigerant flows through the compressor, the condenser, the expansion valve, and the heat exchanger along the refrigerant passage, and according to the change in the state of the refrigerant flowing, the air-conditioner 152 may acquire coldness or warmth. The obtained coldness or warmth may be provided to the interior space of the vehicle 10 through a fan.

The air-conditioner 152 may include a motor configured to drive the fan that generates wind blown into the interior space of the vehicle 10 and adjust a wing member disposed on the blower to adjust the wind direction of blowing wind. In addition, the air-conditioner 152 may include a scent actuator configured to inject a fragrance substance into the air blown into the interior space. The scent actuator may include a plurality of storage tanks for storing various types of aroma substances, an injection port to inject the fragrance substance, and a motor for injecting the fragrance substance through the injection port.

The vibration element 153 according to one exemplary embodiment may vibrate at a predetermined frequency or vibrate at an intensity of a predetermined intensity or higher according to a control signal of the controller 140. The vibration element 153 may be mounted inside a seat 1530 within the vehicle 10 as shown in FIG. 6, but it may be provided without limitation as long as it is at a position allowing the user to feel vibration. The vibration element 153 may be a motor driven by the controller 140. The vibration element 153 may rotate to correspond to the frequency and intensity transmitted from the controller 140, and may transmit the vibration that corresponds to the frequency and intensity transmitted from the controller 140 to the user on the seat. Further, according to the exemplary embodiment, the vibration element 153 may further include a diaphragm for amplifying the vibration.

The lighting device 154 according to an exemplary embodiment may be configured to emit light at a predetermined frequency, emit light at a predetermined brightness, or emit light in a predetermined color according to a control signal of the controller 140. The lighting device 154 may include an interior light disposed on the ceiling of the vehicle 10, a door (not shown) of the vehicle 10, or ambient lighting or the like installed for aesthetic purposes on a part of the dashboard. The description of the display device 170 according to one exemplary embodiment has been described above with reference to FIGS. 5A to 5C, and therefore will be omitted.

Referring to FIG. 7, when the positivity index reaches the target positivity index, the controller 140 may be configured to transmit a control signal for operating the feedback device 150. In particular, the controller 140 may be configured to transmit a control signal for the speaker 151 to output a predetermined sound when the positivity index reaches the target positivity index. The predetermined sound may be a sound that increases the emotion factor corresponding to the positivity. The sound that increases the emotion factor corresponding to the positivity may be predetermined at the design stage and may be a sound having at least one of the loudness level, genre, equalizer, tone and frequency band in which the user feels a positive emotion.

For example, the sound that increases the emotion factor corresponding to the positivity may include hip-hop music, classical music, pop music, etc., where the user may feel the positive emotion. However, the sound that increases the emotion factor corresponding to the positivity may be set based on the user's input through the inputter 130. In other words, the user may set the sound that the individual user relates to the positive emotion as the sound that increases the emotion factor corresponding to the positivity, and the sound that has been set may be stored in the storage 160.

The controller 140 may be configured to transmit at least one of a control signal for the air-conditioner 152 to output a predetermined scent or a control signal for the air-conditioner 152 to output wind of a predetermined mode. The predetermined scent and the wind of the predetermined mode may be a scent and wind that increases the emotion factor corresponding to the positivity. The scent and the mode of the wind may be set in the design stage and may be determined by the controller 140 based on the correlation information between the scent/mode of the wind and the emotion factor, or may be set by the user through the inputter 130.

For example, the scent that increases the emotion factor corresponding to the positivity may be a lemon scent. However, any scent that increases the emotion factor corresponding to the positivity may be included without limitation. In addition, a wind mode for increasing the emotion factor corresponding to the positivity may be an air conditioning mode having at least one of the wind direction, the intensity, and the temperature capable of increasing the positivity. For example, the mode may be a breeze mode or a cool wind mode, but may be included in any mode capable of increasing the emotion factor corresponding to the positivity.

Additionally, the controller 140 may be configured to transmit a control signal for the vibration element 153 to vibrate at a predetermined frequency and/or a control signal for the vibration element 153 to vibrate at a predetermined intensity or more when the positivity index reaches the target positivity index. The predetermined frequency and intensity may be the frequency and the intensity of the vibration, which increase the emotion factor corresponding to the positivity. The vibration frequency that increases the emotion factor corresponding to the positivity may include a frequency higher than the frequency of the user's bio-signals and may be a frequency corresponding to the frequency of the sound that increases the emotion factor corresponding to the positivity, however the vibration frequency may be determined as any frequency that increases the emotion factor corresponding to the user's positivity without limitation.

The frequency and the intensity that increase the emotion factor corresponding to the positivity may be set at the design stage and may be determined by the controller 140 based on the correlation information between the vibration frequency/intensity and the emotion factor, or may be set by the user through the inputter 130. The controller 140 may also be configured to transmit a control signal for the lighting device 154 to emit light at a predetermined frequency and/or a control signal for the lighting device 154 to emit light at a predetermined brightness and/or a control signal for the lighting device 154 to emit light in a predetermined color when the positivity index reaches the target positivity index. The predetermined frequency, brightness, and color may be the frequency, brightness, and color that increase the emotion factor corresponding to the positivity.

The light frequency that increases the emotion factor corresponding to the positivity may include a frequency higher than the frequency of the user's bio-signals and may be a frequency corresponding to the frequency of the sound that increases the emotion factor corresponding to the positivity, however the light frequency may be determined as any frequency that increases the emotion factor corresponding to the user's positivity without limitation. The frequency, the brightness and the color that increase the emotion factor corresponding to the positivity may be set at the design stage and may be determined by the controller 140 based on the correlation information between the light frequency/brightness/color and the emotion factor, or may be set by the user through the inputter 130. The controller 140 may be configured to transmit the control signal for the display device 170 to display a predetermined image when the positivity index reaches the target positivity index. This has been described above in detail with reference to FIGS. 5A to 5C, and will not be described here.

Figure 8:
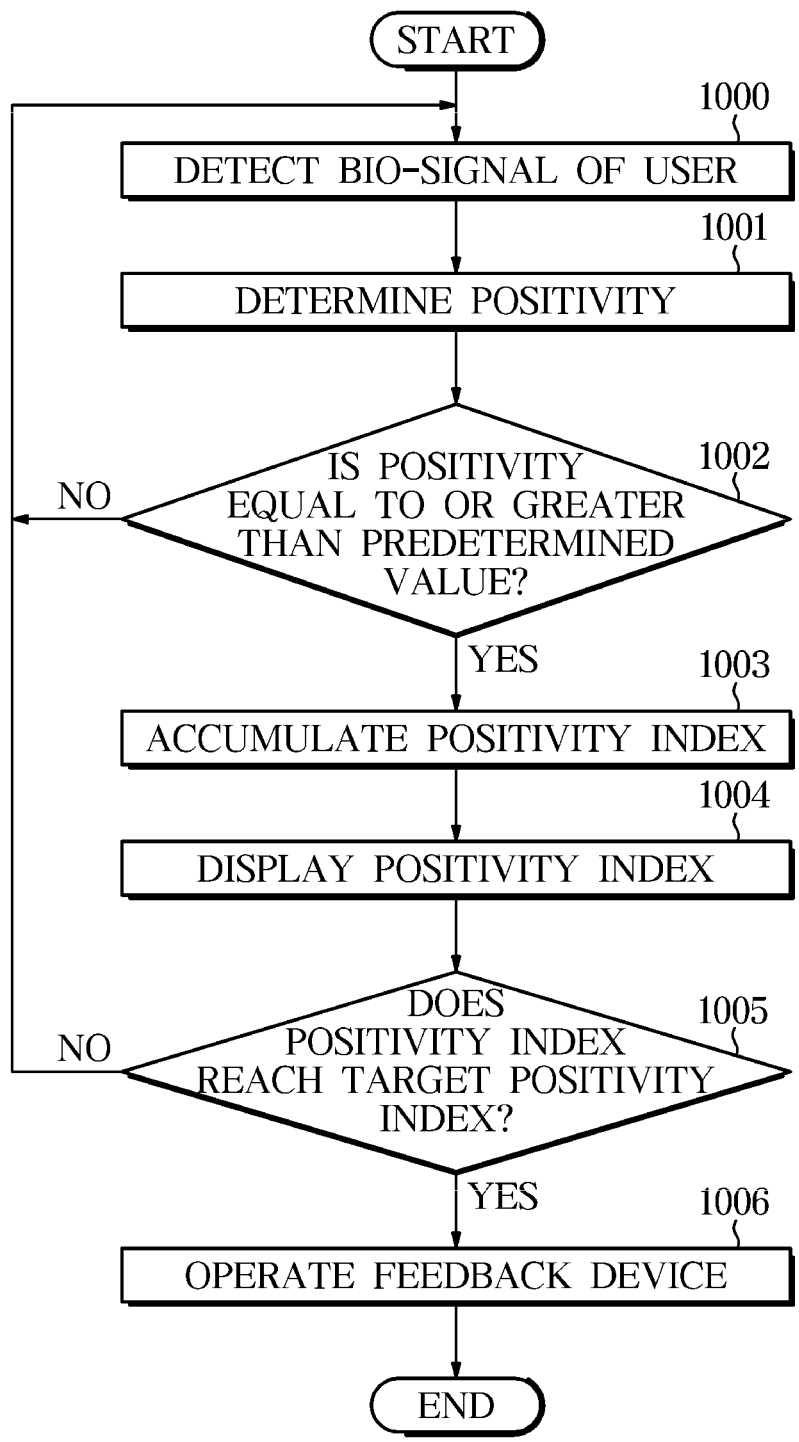
FIG. 8 is a flowchart illustrating a vehicle control method according to an exemplary embodiment of the present disclosure.

Hereinafter, a control method of the vehicle 10 according to the exemplary embodiment will be described with reference to FIG. 8. The method described herein below may be executed by a controller of the vehicle. Referring to FIG. 8, the bio-signal sensor 120 may be configured to detect a bio-signal of the user (1000). The bio-signal indicates a signal capable of detecting the physical condition and the mental state of the user. For example, the bio-signal may be a respiration or a pulse of the user. Various sensors for detecting bio-signals are already described above.

The controller 140 may then be configured to determine at least one of a positivity of the user or change amount of the positivity of the user based on the detected bio-signal (1001). The specific manner in which the controller 140 determines at least one of the degree of positivity of the user and the amount of change of the positivity is as described above with reference to FIGS. 1 to 4.

Further, the controller 140 may be configured to determine whether the positivity is equal to or greater than a predetermined positivity or the change amount of the positivity is equal to or greater than a predetermined change amount of the positivity (1002). When the positivity is less than a predetermined positivity and the change amount of the positivity is less than a predetermined change amount of the positivity, the process may return to detecting the bio-signal of the user (1000). When the positivity is equal to or greater than the predetermined positivity or the change amount of the positivity is equal to or greater than the predetermined change amount of the positivity, the controller 140 may be configured to accumulate a positivity index (1003).

The controller 140 may then be configured to transmit a control signal for display device 170 to display the positivity index of the user as described above, and display the positivity index of the user according to the control signal (1004). However, it should be understood that the step of displaying the positivity index by the display device 170 is not a temporary step, but rather a continuous step while the vehicle 10 is operating. In other words, it should not be limited to the step performed after the positivity index of the user is accumulated (1003).

The controller 140 may be configured to determine whether the positivity index reaches the target positivity index. When the positivity index does not reach the target positivity index, the process may return to detecting the bio-signal of the user (1000). When the positivity index reaches the target positivity index, the controller 140 may be configured to transmit a signal to the feedback device 150 to operate the feedback device 150.

The detailed method of transmitting the control signal for operating the feedback device 150 is as described above, and the feedback device 150 may include the speaker 151, the air-conditioner 152, the vibration elements 153, and the lighting device 154 as described above. When the controller 140 operates the feedback device 150, which means when the positivity index reaches the target positivity index, the entire procedure may be terminated and the procedure may be repeated from first step. In particular, the controller 140 may be configured to reset the positivity index to the initial value.

Figure 9:
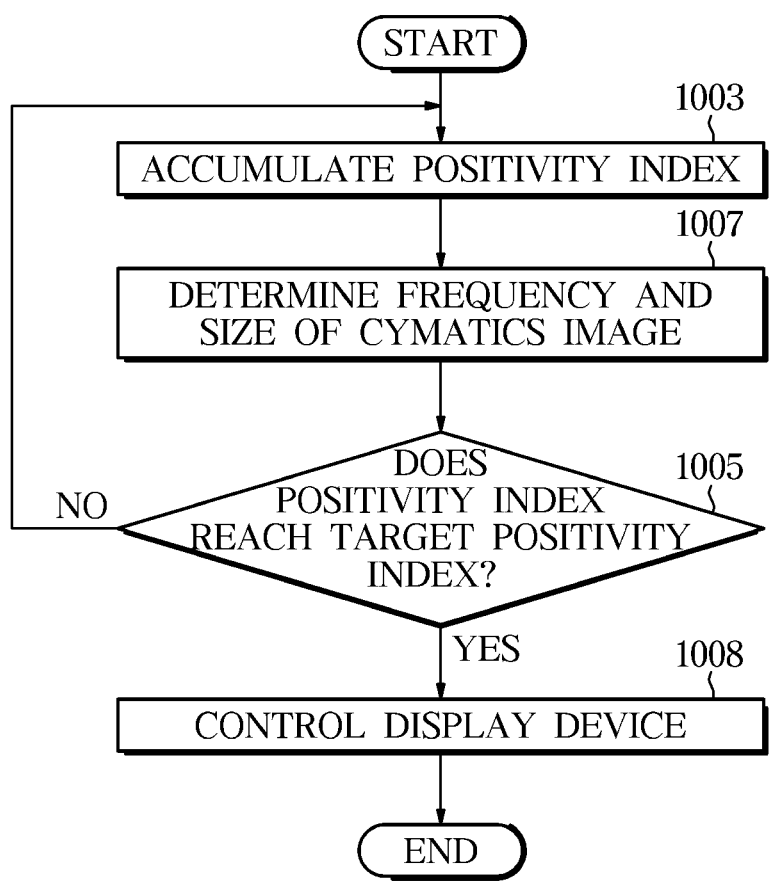
FIG. 9 is a part of a flowchart illustrating a vehicle control method according to an exemplary embodiment of the present disclosure.

FIG. 9 is a part of a flowchart illustrating a vehicle control method according to an exemplary embodiment of the present disclosure. Referring to FIG. 9, the controller 140 may be configured to determine at least one of the frequency or size of the cymatics image based on the positivity index, for example in proportion to the positivity index (1005), and transmit a control signal to the display device 170 to display the cymatics image having at least one of the determined frequency or size, and display the cymatics image according to the control signal of the controller 140. The specific manner in which the controller 140 determines the frequency and size of the cymatics image is as described above.

Additionally, the controller 140 may be configured to determine whether the positivity index reaches the target positivity index. When the positivity index does not reach the target positivity index, the process may return to detecting the bio-signal of the user (1000). When the positivity index reaches the target positivity index, the controller 140 may be configured to transmit a signal to the display device 170 to display the predetermined image (1008). The specific method is as described above. When the controller 140 operates the display device 170, which means when the positivity index reaches the target positivity index, the entire procedure may be terminated and the procedure may be repeated from first step. In particular, the controller 140 may be configured to reset the positivity index to the initial value.

The vehicle and control method thereof according to an exemplary embodiment of the present invention may induce and maximize the positive emotion of the users by determining the positivity of the users in the vehicle, accumulating the positivity index based on the positivity, and rewarding the users when the positivity index reaches the target positivity index.

Exemplary embodiments of the present disclosure have been described above. In the exemplary embodiments described above, some components may be implemented as a "module." Here, the term 'module' means, but is not limited to, a software and/or hardware component, such as a Field Programmable Gate Array (FPGA) or Application Specific Integrated Circuit (ASIC), which performs certain tasks. The module may advantageously be configured to reside on an addressable storage medium and configured to execute on one or more processors.

Thus, the module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The operations provided for in the components and modules may be combined into fewer components and modules or further separated into additional components and modules. In addition, the components and modules may be implemented such that they execute one or more CPUs in a device.

With that being said, and in addition to the above described exemplary embodiments, embodiments may thus be implemented through computer readable code/instructions in/on a medium, e.g., a non-transitory computer readable medium, to control at least one processing element to implement any of the above described exemplary embodiments. The medium may correspond to any medium/media permitting the storing and/or transmission of the computer readable code.

The computer-readable code may be recorded on a medium or transmitted through the Internet. The medium may include Read Only Memory (ROM), Random Access Memory (RAM), Compact Disk-Read Only Memory (CD-ROM), magnetic tapes, floppy disks, and optical recording medium. Also, the medium may be a non-transitory computer-readable medium. The media may also be a distributed network, so that the computer readable code is stored or transferred and executed in a distributed fashion. Still further, as only an example, the processing element could include at least one processor or at least one computer processor, and processing elements may be distributed and/or included in a single device.

While exemplary embodiments have been described with respect to a limited number of embodiments, those skilled in the art, having the benefit of this disclosure, will appreciate that other exemplary embodiments can be devised which do not depart from the scope as disclosed herein. Accordingly, the scope should be limited only by the attached claims.

What is claimed is:

1. A vehicle, comprising:
   a bio-signal sensor configured to detect a bio-signal of a user;

a display device configured to display an image; and
a controller configured to
　determine at least one of a positivity of the user or change amount of the positivity of the user based on the detected bio-signal,
　accumulate a positivity index when at least one of the positivity or change amount of the positivity is equal to or greater than a predetermined positivity or a predetermined change amount of the positivity, and
　transmit a control signal to the display device to display the accumulated positivity index,
　wherein the display device is configured to display a cymatics image which is transformed according to a frequency, and the controller is configured to determine at least one of a frequency or size of the cymatics image in proportion to the positivity index, and transmit a control signal to the display device to display the cymatics image having at least one of the determined frequency or size.

2. The vehicle according to claim 1, wherein: the controller is configured to transmit a control signal to the display device to display a predetermined image when the positivity index reaches a target positivity index.

3. The vehicle according to claim 1, further comprising:
a feedback device configured to operate to increase the positivity of the user;
wherein the controller is configured to transmit a signal to the feedback device to operate when the positivity index reaches a target positivity index.

4. The vehicle according to claim 3, wherein the feedback device includes vibration elements disposed on a seat of the vehicle, and the controller is configured to transmit at least one of a control signal for the vibration elements to vibrate at a predetermined frequency or a control signal for the vibration elements to vibrate at a predetermined intensity or more.

5. The vehicle according to claim 3, wherein the feedback device includes a speaker disposed within the vehicle, and the controller is configured to transmit a control signal for the speaker to output a predetermined sound.

6. The vehicle according to claim 3, wherein the feedback device includes a lighting device disposed within the vehicle, and the controller is configured to transmit at least one of a control signal for the lighting device to emit light at a predetermined frequency, a control signal for the lighting device to emit light at a predetermined brightness, or a control signal for the lighting device to emit light in a predetermined color.

7. The vehicle according to claim 3, wherein the feedback device includes an air-conditioner disposed within the vehicle, and the controller is configured to transmit at least one of a control signal for the air-conditioner to output a predetermined scent or a control signal for the air-conditioner to output wind of a predetermined mode.

8. The vehicle according to claim 1, wherein the controller is configured to reset the positivity index to an initial value when the positivity index reaches a target positivity index.

9. The vehicle according to claim 1, further comprising:
a camera configured to obtain image data for the user;
wherein the controller is configured to determine the positivity of the user based on at least one of the image data for the user or the bio-signal of the user.

10. The vehicle according to claim 1, further comprising:
an inputter configured to receive information of at least one of an initial value of the positivity index or a cumulative condition of the positivity index.

11. The vehicle according to claim 1, wherein the controller is configured to transmit the control signal for the display device to display the accumulated positivity index in a form of at least one of a numeral, an emoticon indicating an emotional state, gauge bar, or a letter.

12. A vehicle control method, comprising:
detecting, by a controller, a bio-signal of a user using a sensor;
determining, by the controller, at least one of a positivity of the user or change amount of the positivity of the user based on the detected bio-signal;
accumulating, by the controller, a positivity index when at least one of the positivity or change amount of the positivity is equal to or greater than a predetermined positivity or a predetermined change amount of the positivity; and
displaying, by the controller, the accumulated positivity index,
further comprising:
determining, by the controller, at least one of a frequency or size of a cymatics image in proportion to the positivity index; and
displaying, by the controller, the cymatics image having at least one of the determined frequency or size.

13. The vehicle control method according to claim 12, further comprising:
displaying, by the controller, a predetermined image when the positivity index reaches a target positivity index.

14. The vehicle control method according to claim 12, further comprising:
transmitting, by the controller, a control signal to operate a feedback device when the positivity index reaches a target positivity index.

15. The vehicle control method according to claim 14, wherein the feedback device includes vibration elements disposed on a seat of a vehicle, and the transmitting of the control signal for operating the feedback device when the positivity index reaches the target positivity index includes:
transmitting, by the controller, at least one of a control signal for the vibration elements to vibrate at a predetermined frequency or a control signal for the vibration elements to vibrate at a predetermined intensity or more.

16. The vehicle control method according to claim 14, wherein the feedback device includes a speaker disposed within a vehicle, and the transmitting of the control signal for operating the feedback device when the positivity index reaches the target positivity index includes:
transmitting, by the controller, a control signal for the speaker to output a predetermined sound.

17. The vehicle control method according to claim 14, wherein the feedback device includes a lighting device disposed within a vehicle, and the transmitting the control signal for operating the feedback device when the positivity index reaches the target positivity index includes:
transmitting, by the controller, at least one of a control signal for the lighting device to emit light at a predetermined frequency, a control signal for the lighting device to emit light at a predetermined brightness, or a control signal for the lighting device to emit light in a predetermined color.

18. The vehicle control method according to claim 14, wherein the feedback device includes an air-conditioner disposed in a vehicle, and the transmitting of the control signal for operating the feedback device when the positivity index reaches the target positivity index includes:

transmitting, by the controller, at least one of a control signal for the air-conditioner to output a predetermined scent or a control signal for the air-conditioner to output wind of a predetermined mode.

* * * * *